United States Patent [19]

Hecht et al.

[11] Patent Number: 4,923,813

[45] Date of Patent: May 8, 1990

[54] MONOCLONAL ANTIBODY-BASED IMMUNOASSAY FOR CYCLIC DNA ADDUCTS RESULTING FROM EXPOSURE TO CROTONALDEHYDE OR ACROLEIN

[75] Inventors: Stephen S. Hecht, Larchmont; Peter G. Foiles, Croton-on-Hudson; Fung-Lung Chung, Yorktown Heights, all of N.Y.

[73] Assignee: American Health Foundation, Valhalla, N.Y.

[21] Appl. No.: 144,490

[22] Filed: Jan. 15, 1988

[51] Int. Cl.$^5$ ............................................. G01N 33/577
[52] U.S. Cl. .......................... 435/172.2; 435/240.27; 435/948; 436/548; 436/813; 436/822; 530/387; 530/809; 935/104; 935/110
[58] Field of Search ............... 435/172.2, 240.27, 948; 436/543, 548, 813, 822; 935/104, 110; 530/387, 807, 809

[56] References Cited

U.S. PATENT DOCUMENTS 4,794,074 12/1988 Harris ................................ 436/501

OTHER PUBLICATIONS

Chung et al, *Cancer Research*, 43, 1230-1235, 1983.
Erlanger, *Meth. Enzymol.*, 70, 88-89, 1980.
Foiles et al, *Chem. Abstr.*, 106, Abstr. No. 133152e, 1987.
Hertzog et al, *Journ. Immun. Meth.*, 62, 49-58, 1983.
Poirier et al, *Nature* (London), 270, 186, 1977.

*Primary Examiner*—Robert J. Warden
*Assistant Examiner*—David A. Saunders
*Attorney, Agent, or Firm*—Ladas & Parry

[57] ABSTRACT

Monoclonal antibodies specific for the 8R,6R- and 8S,6S-stereoisomers of 3-(2-deoxy-β-D-erythropentofuranosyl)-5,6,7,8-tetrahydro-8-hydroxy-6-methyl-pyrimido[1,2-a]purine-10(3H)one were produced. These cyclic 1,$N^2$-propanodeoxyguanosines are formed in DNA exposed to crotonaldehyde in vitro. Three of the four antibodies were most specific for one stereoisomer while the fourth was most specific for the other stereoisomer. Fifty % inhibition of binding in an enzyme-linked immunoabsorbent assay could be achieved with 0.2 picomol of either stereoisomer. A high-pressure liquid chromatography-enzyme-linked immunoabsorbent assay using two of these antibodies and capable of detecting 0.5 μmol of 1,$N^2$-propanodeoxyguanosine per mol of deoxyguanosine was developed. The method was validated by comparison to results obtained with fluorescence assay.

3 Claims, 4 Drawing Sheets

FIG. 1A
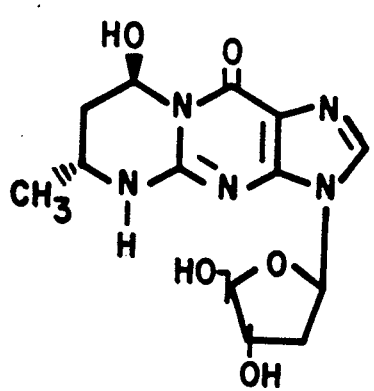
FIG. 1B
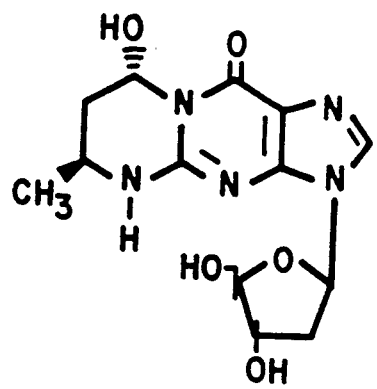
FIG. 1C
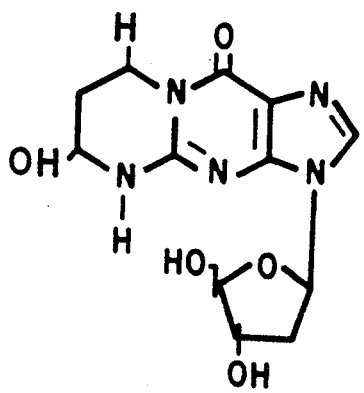
FIG. 1E
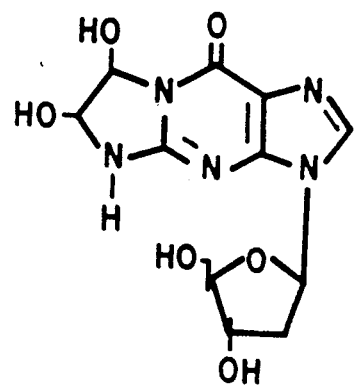
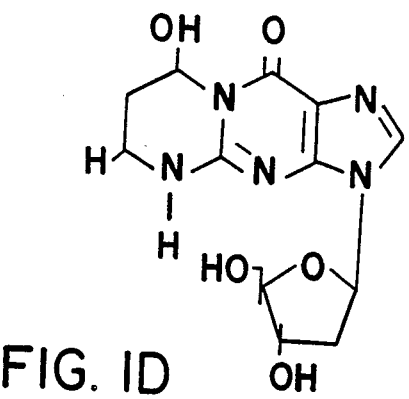
FIG. 1D

MONOCLONAL ANTIBODY-BASED IMMUNOASSAY FOR CYCLIC DNA ADDUCTS RESULTING FROM EXPOSURE TO CROTONALDEHYDE OR ACROLEIN

FIELD OF INVENTION

This invention relates to an immunoassay for DNA modifications resulting from exposure to crotonaldehyde or acrolein and more particularly to the development of monoclonal antibodies specific for certain cyclic deoxyguanosine adducts.

BACKGROUND OF THE INVENTION

In an effort to develop sensitive and precise probes with which to investigate the biochemical and biological consequences of carcinogen-induced genomic damage, scientists have elicited animal antibodies against carcinogen-DNA adducts. (Poirier, M. C. "The Use of Carcinogen-DNA Adduct Antisera for Quantitation and Localization of Genomic Damage in Animal Models and the Human Population", Environmental Mutagenesis 6:879–887 (1984)). The use of antibodies to detect chemical carcinogen-induced DNA damage involves quantitative determination using antisera specific for carcinogen-DNA adducts.

In recent years immunoassays for a variety of carcinogen-DNA adducts have been developed, many involving the use of monoclonal antibodies. (Wild, C. P., Smart G., Saffhill, R., and Boyle J. M. Radioimmunoassay of $O^6$-methyldeoxyguanosine in DNA of cells alkylated in vitro and in vivo. Carcinogenesis (Lond.), 4: 1605–1609, 1983; Hsu, I-C., Poirier, M. C. Yuspa, S. H. Grunberger, D., Weinstein, I. B., Yolken, R. H., and Harris, C. C. Measurement of benzo(a)pyrene-DNA adducts by enzyme immunoassay and radioimmunoassay. Cancer Res., 41: 1091–1095, 1981; Groopman, J. D., Haugen, A., Goodrich, G. R., Wogan, G. N., and Harris, C. C. Quantitation of aflatoxin $B_1$-modified DNA using monoclonal antibodies, Cancer Res., 42: 3120–3124, 1982; Poirier, M. C. The use of carcinogen-DNA adduct antisera for quantitation and localization of genomic damage in animal models and the human population. Environ. Mutagen., 6: 879–887, 1984). Preparation of monoclonal antibodies able to detect particular antigens and for the production by hybridoma technology of pure antibodies is well-known in the art. These assays are highly sensitive being able to detect as little as 0.5 $\mu$mol adduct per mol deoxyguanosine. Carcinogen-DNA adducts have also been detected in humans with the aid of immunoassays. (Harris, C. C., Vahakangas, K., Newman, M. J., Tivers, G. E., Shamsuddin, A., Sinopoli, N., Mann, D. L., and Wright, W. E., Detection of benzo(a)pyrene diol epoxide-DNA adducts in peripheral blood lymphocytes and antibodies to the adducts in serum from coke oven workers, Proc. Natl. Acad. Sci. USA, 82: 6672–6676, 1985; Umbenhauer, D., Wild, C. P., Montesano, R., Saffhill, R., Boyle, J. M., Huh, N., Kirstein, U., Thomale, J., Rajewsky, M. F., and Lu, S. H., $O^6$-Methyldeoxyguanosine in oesphageal DNA among individuals at high risk of oesophageal cancer. Int. J. Cancer, 36: 661–665, 1985.)

Notwithstanding the above, a problem with immunoassays is the production of a suitable antibody. If one is interested in detecting and measuring a specific DNA adduct, there is little point in eliciting antibodies against a different albeit related molecule. Furthermore, while the limits of sensitivity and specificity are theoretically high, in practice obtaining suitable antibodies is a rare event.

Indeed, although the technique underlying hybridoma technology is well recognized, nevertheless, the results obtained by its use clearly are unpredictable. Hybridoma technology is an empirical art in which the routinist is unable to foresee what particular antibodies will be produced and which specific surface antigens will be recognized by them. Only by actually carrying out the requisite steps can the nature of the monoclonal antibodies be determined and ascertained.

Recently the modified nucleosides 8R, 6R- and 8S, 6S-3-(2-deoxy-3-$\beta$-erythro-pentofuranosyl) 5, 6, 7, 8-tetrahydro-8-hydroxy-6-methylpyrimido(1, 2-a)purine-10(3H)one were identified in DNA which had been exposed in vitro to crotonaldehyde ($CH_3CH=CHCHO$). The same modified deoxyguanosines may also form as a result of hydroxylation of N-nitrosopyrrolidine (NPYR). Both crotonaldehyde and NPYR are tumorigenic in rats with NPYR being the more potent of the two. Crotonaldehyde is also mutagenic toward Salmonella typhimurium and is commonly found in the human environment. NPYR is found in cooked bacon, mainstream and sidestream tobacco smoke, and as a trace contaminant of various foodstuffs.

In order to study the role of the cyclic DNA adducts in the mechanism of action of crotonaldehyde and NPYR a sensitive assay was heretofore needed to measure the formation of such adducts.

SUMMARY OF THE INVENTION

It is an object of the invention to develop an immunoassay for cyclic DNA adducts resulting from exposure of DNA to crotonaldehyde or acrolein.

It is another object of the invention to develop a process for the preparation of monoclonal antibodies specific for such DNA adducts.

It is a further object of the invention to prepare antibody-producing hybridoma cell lines characterized by the production of monoclonal antibodies specific for such DNA adducts.

Still a further object of the invention is the preparation of an inoculum which will raise antibodies in an animal which will be useful in detecting the presence of such DNA adducts.

In accordance with the above and other objects of the invention, there is provided a process comprising preparing monoclonal antibodies specific for DNA modifications resulting from exposure of DNA to crotonaldehyde or acrolein. The process comprises
  i. reacting deoyguanosine with crotonaldehyde or acrolein to form a cyclic deoxyguanosine adduct;
  ii. coupling the adduct to a protein to form an adduct-conjugate;
  iii. immunizing an animal with the conjugate;
  iv. harvesting the immunized animal's lymphocytes;
  v. fusing the lymphocytes with a cell which is capable of reproducing itself in cell cultures;
  vi. screening the fused cells for the production of antibody specific for the cyclic adduct;
  vii. identifying, isolating and cloning the fused cells which test positive for the production of monoclonal antibody.

In a specific embodiment of the invention, the carcinogen is crotonaldelyde and the adduct consists of the 8R, 6R- and 8S, 6S-stereoisomers of 3-(2-deoxy-B-D-erythropentofuransoyl)-5, 6, 7, 8-hydroxy-6-methylpyrimido (1, 2-a)purine-10(3H)one. The protein to which the cyclic deoxyguanosine adduct is conjugated is keyhole limpet hemocyanin in a preferred embodiment. The animal immunized with the conjugate may be a BALB/c×C57BL/6F$_1$ mouse. The monoclonal antibodies prepared in accordance with the invention may be used to assay for the presence of the adduct by reacting the monoclonal antibody with a sample of DNA to be tested.

Also in accordance with the invention, there is provided monoclonal antibodies recognizing at least one of the 8R, 6R- and 8S, 6S-stereoisomers of 3- (2-deoxy-B-D-erythro-pentofuranosyl)-5, 6, 7, 8-tetrahydro-8-hydroxy-b-methylpyrimidol(1, 2-a) purine-10(3H)one. These antibodies may be selected from the group of antibodies produced by hybridoma cell lines deposited with American Type Culture Collection depository and named HB9621; HB9622; HB9623 and HB9624.

In accordance with the invention there is further provided antibody producing hybridoma cell lines characterized by the production of monoclonal antibodies recognizing cyclic deoxyguanosine adducts. These hybridoma cell lines are selected from the group consisting of HB9621; HB9622; HB9623 and HB9624.

The invention still further provides for a conjugate useful in the immunization of mice for production of antibodies specific for DNA modifications resulting from exposure of the DNA to crotonaldehyde. The conjugate comprises KLH and the ribose forms of cyclic deoxyguanosine adducts selected from the group consisting of the 8R, 8S, 6S-stereoisomers of 3-(2-deoxy-$\beta$-D-erythro-pentofuranosyl)-5, 6, 7, 8-tetrahydro-8-hydroxy-6-methylpyrimido(1, 2-a)purine-10(3H)one.

BRIEF DESCRIPTION OF THE DRAWINGS

These and other object and features of the present invention will readily be understood from the following description taken in conjunction with a preferred embodiment thereof with reference to the accompanying drawings, in which:

FIG. 1 is a depiction of cyclic deoxyguanosine adducts formed by reaction of DNA with crotonaldehyde (structures 1a and 1b); acrolein (structures 1c and 1d); and glyoxal (structure 1e);

DETAILED DESCRIPTION

Figure 2A:
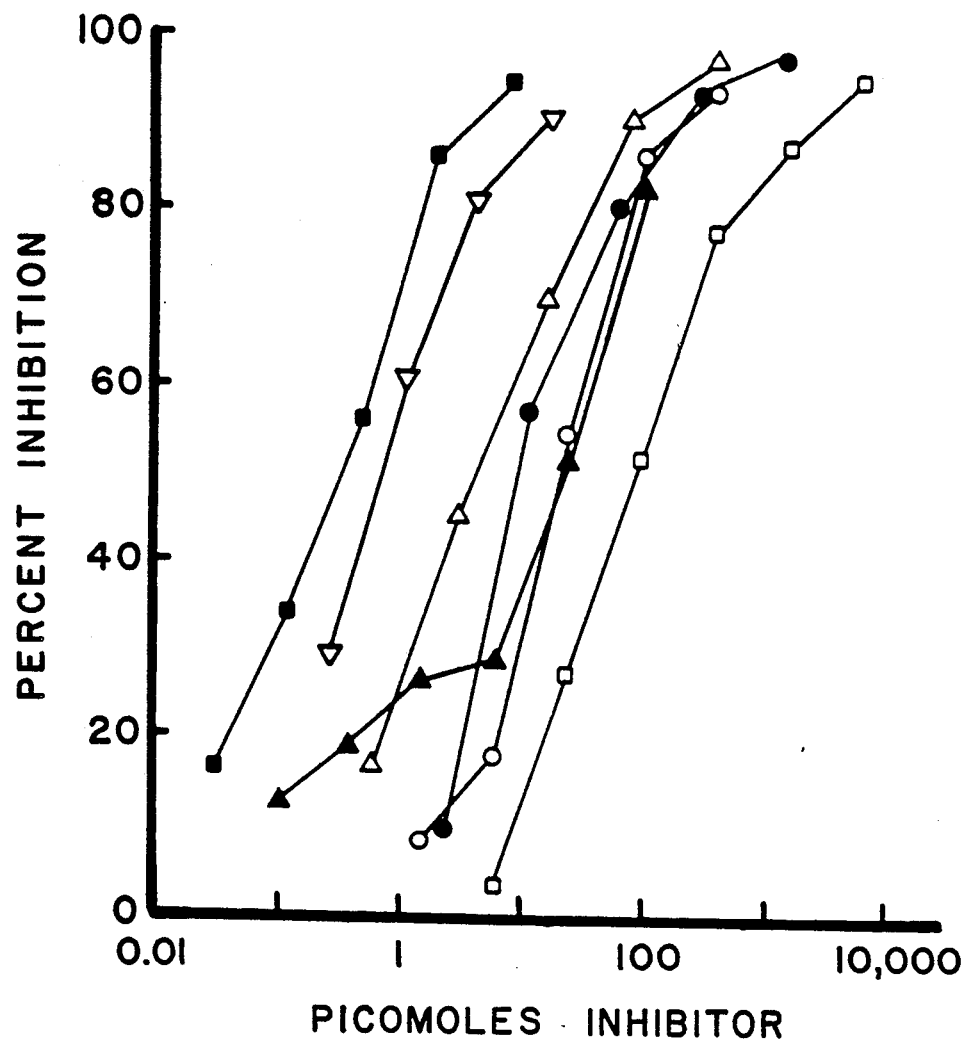
FIG. 2 comprises graphs 2a and 2b showing the binding specificities of antibodies produced using the process of the invention with the structures shown in FIG. 1.

In order to develop an immunoassay for DNA modifications resulting from exposure of DNA to crotonaldehyde, acrolein or glyoxal respectively, the structures shown in FIG. 1 are first synthesized. Structures 1a and 1b in FIG. 1 show the cyclic deoxyguanosine adducts formed by reaction of DNA with crotonaldehyde. Structures 1c and 1d of FIG. 1 show the cyclic deoxyguanosine adducts formed by reaction of DNA with acrolein. Structure 1e of FIG. 1 shows the cyclic deoxyguanosine adducts formed by reaction of DNA with glyoxal.

The synthesis of these adducts are known in the art as shown, for example, by the following publications which describe the synthesis of structures formed by DNA modifications resulting from exposure to crotonaldehyde, acrolein and glyoxal respectively:

(1) Chung, F. L., and Hecht, S. S. Formation of cyclic 1, N$^2$ adducts by reaction of deoxyguanosine with $\alpha$-acetoxy-N-nitrosopyrrolidine, 4-(carbethoxynitrosamino) butanal, or crotonaldehyde. Cancer Res., 43: 1230–1235, 1983 (hereinafter called "Chung-Hecht 1").

(2) Chung, F. L., and Young, R., and Hecht, S. S. Formation of cyclic 1, N2-propanodeoxyguanosine adducts in DNA upon reaction with acrolein or crotonaldehyde. Cancer Res., 44 990–995, 1984.

(3) Chung, F. L., and Hecht, S. S. Formation of the cyclic 1, N$^2$-glyoxal-deoxyguanosine adduct upon reaction of N-nitroso-2-hydroxymorpholine with deoxyguanosine. Carcinogenesis (Lond.) 6: 1671–1673, 1985.

In a preferred embodiment of the invention, Calf thymus DNA (Sigma Chemical Co., St. Louis, Mo.) is modified in vitro with crotonaldehyde as follows. Twenty mg. of DNA is dissolved in 4 ml of 0.1 M phosphate buffer (pH 7.0). Forty-five mg of crotonaldehyde (Aldrich Chemical Co., Milwaukee, Wis.) are added and the mixture is incubated in a 37° C. shaking water bath for 48 h. The DNA is then precipitated with cold ethanol, redissolved, and reprecipitated three time. The modified DNA is stored at −20° C.

Coupling of Adduct to Protein. The ribose forms of structures 1a and 1b are synthesized by the reaction of crotonaldehyde with guanosine, under conditions known in the art and described, by way of example, in Chung-Hecht (1). The structures of the guanosine adducts may be confirmed by their UV spectra. These should be identical to those of structures 1a and 1b. Their proton nuclear magnetic resonance spectra will show characteristic chemical shifts for the ribosyl protons and the 1,N-propanoguanine protons. The diastereomers are then coupled to KLH using the periodate oxidation method known in the art and described, for example, by Meredith and Erlanger in Meredith, R. D., and Erlanger, B. F. Isolation and characterization of rabbit anti-m7 G-5'-P antibodies of high apparent affinity. Nucleic Acids Res., 6: 2179–2191, 1979.

Crotanaldehyde-guanosine adduct may be prepared by dissolving 2 gm of guanosine in 200 ml of phosphate buffer, pH 7.0. Crotonaldehyde (8.4 gm) may be added and the mixture incubated at 37° C. with shaking for 2 h. Another 4.2 gm of crotonaldehyde may be added and the reaction continued for an additional 1 h. The reaction mixture may then be extracted 3 times with 50 ml of methylene chloride and the aqueous phase concentrated to 30 ml by rotary evaporation. Methanol may be added until the solution becomes cloudy. After standing at room temperature for 1 h an oil may separate which can be discarded. Silica gel may be added to the aqueous solution and the suspension brought to dryness by rotary evaporation. The residue may be applied to the top of a dry packed silica gel column. The column may be eluted with methylene chloride:methanol (4:1), and fractions examined by thin-layer chromatography on silica with development by methylene chloride:methanol:ammonium hydroxide (95:15:2). Fractions containing the adducts may be combined and final purification made by HPLC using a 50 cm×9.4 mm Partisil ODS-3 Magnum-9 column programmed from 0 to 20%

MeOH in 50 min using a linear gradient and a flow rate of 5 ml/min.

The crotonaldehyde-guanosine adduct may be coupled to bovine serum albumin (BSA) by dissolving 2 mg in 200 ul of ice cold 0.1M sodium periodate. The pH may be titrated to 5.0 with 10% acetic acid and the mixture stirred on ice for 20 min. The periodate oxidized adduct may be added to 10 mg of BSA dissolved in 1 ml of saline. The pH may be adjusted to 8.0 with 10% potasium carbonate and stirred on ice for 20 min. Sodium cyanoborohydride (150 ul of a 0.25% solution) may then be added and the pH adjusted to 6.5–7.0 with 10% acetic acid and the solution stirred on ice for 40 min. The conjugate may then be dialyzed extensively against saline and stored frozen $-20°$ C.

Immunization. Female BALB/c $\times$ C57BL/6F$_1$ mice are immunized with 100 $\mu$g of structure 1$a,b$-KLH conjugate in 0.1 ml of saline emulsified with an equal volume of Freund's complete adjuvant, given in a split dose, i.p. and s.c. A second injection is given at 2 weeks in incomplete Freund's adjuvant. Four weeks after the second injection individual mice may be boosted with 100 $\mu$g of conjugate in saline given i.p. on days 1, 2, 3, and 4. On day 5 the mouse may be sacrificed and the spleen removed for fusion.

Fusion Protocol. Protocols for fusing the immunized mouse's cells with cells which are capable of reproducing themselves in cell cultures are known. See, for example, Fazekas de St. Groth, S., and Scheidegger, D. Production of monoclonal antibodies; strategy and tactics. J. Immunol. Methods, 35: 1–21, 1980. A fusion partner OF is maintained in RPMI 1640 supplemented with 1 mM sodium pyruvate, 25 $\mu$g/ml gentamicin, and 15% fetal bovine serum. The FO cells are maintained in logphase growth for 3 days prior to fusion. The FO cells are centrifuged and resuspended in Hank's balanced salt solution (HBSS). A single cell suspension is made by forcing the spleen through a fine mesh stainless steel screen followed by centrifugation. RBC are lysed by resuspending the cell pellet in 5 ml of cold Tris-ammonium chloride (9 parts 0.83% NH$_4$Cl, 1 part 170 mM Tris, pH 7.2) and incubating for 5 min. on ice. The cells are washed, resuspended in 10 ml of HBSS, and counted. The spleen cells are mixed with the FO cells at a ratio of 5:1 in a 17$\times$100-mm polypropylene test tube (Falcon Labware, Oxnard, Calif.: 2006) and centrifuged. The liquid is removed from the pellet and 1 ml of the fusing solution (50% HBSS, 45% polyethylene glycol (Eastman Kodak Co., Rochester, N.Y.; M 1450) and 5% dimethyl sulfoxide) is added. The cell pellet is broken into small clumps by gentle agitation and incubated for 5 min. at 37° C. The fused cells are centrifuged and the supernatant is discarded. The cells are resuspended in 5 ml of complete RPMI 1640 and centrifuged, and the cell pellet is resuspended in 50 ml of complete RPMI 1640 supplemented with hypoxanthine (0.1 mM), aminopterin (0.4 M), thymidine (16 $\mu$M), insulin (5 $\mu$g/ml), transferrin (5 $\mu$g/ml), and sodium selenite (5 ng/ml). The cells may be cultured in 96-well tissue culture plates at 150 $\mu$l well and incubated at 37° C. in 5% CO$_2$ in air. On day 6 the cultures may be fed with 50 $\mu$l of complete RPMI 1640 supplemented with hypoxanthine and thymidine. By day 14 the colonies should be sufficiently large to be screened for antibody production.

Screening for Antibody Production. In order to screen the fused cells for the production of antibody specific for the cyclic deoxyguanosine adducts, an enzyme-linked immunosorbent assay ("ELISA") may be used. ELISA links soluble antigens to insoluble antibodies or soluble antibodies to solid phase antigens in a manner that allows both immunolgical and enzymatic activity to be retained.

ELISA techniques for antigen or antibody quantification are well-known to the art. By way of example, wells of a 96-well polystyrene ELISA plate may be coated with 10 ng of structure $a$, $b$-KLH conjugate, diluted in Phosphate buffered saline (PBS), for 1 h at room temperature. The wells may be washed twice with PBS containing 0.1% Tween 20 and twice with distilled H$_2$O. From this point all reagents may be diluted in PBS containing 0.1% bovine serum albumin ("BSA"). Wells are filled with 50 $\mu$l of PBS-BSA followed by 50 $\mu$l of culture supernatant and incubated at room temperature for 1 h. For competitive ELISA, adduct standards or test samples are mixed with the monoclonal antibody and added to the well. The wells are washed and 100 $\mu$l of alkaline phosphatase-labeled goat anti-mouse 1 gG antibody (Kirkegaard & Perry Laboratories, Inc., Gaithersburg, Md.) are added to each well and incubated at room temperature for 1 h. After washing, 100 $\mu$l of substrate solution (1 mg/ml of p-nitrophenylphosphate in 1M diethanolamine buffer, pH 9.8) are added to each well and incubated at room temperature for 30 min. The reaction is stopped by the addition of 50 $\mu$l of 60 mM EDTA and the absorbance at 405 nm may be read with a Bio-Tek EL-308 ELISA reader (Bio-Tek Instruments, Burlington, Vt.). In quantitative experiments the concentration of unknown samples may be determined by comparison to a standard curve relating the log of the inhibitor concentration to the logit of the percentage of inhibition $$\log \frac{\% \text{ of inhibition}}{100\% - \% \text{ of inhibition}}$$

Cloning of Hybridomas. Hybrid cultures which are positive in the ELISA screening test may be cloned by limiting dilution in hanging drop cultures by known procedures such as those described by Bell et al. in Bell, E. B., Brown, M., and Rittenberg, M. B. In vitro antibody synthesis in 20 ml hanging drops: initiation of secondary responses and a simple method of cloning hybridomas. J. Immunol, Methods, 62: 137–145, 1983. Drops with viable colonies may be selected microscopically and transferred to a 96-well culture plate and expanded. The class and subclass of the antibodies may be determined by using a subisotyping kit from, for example, HyClone Laboratories (Logan, Utah).

DNA Adduct Immunoassay. An assay of DNA samples for the presence of adduct may be performed by enzyme hydrolyzing 1–2 mg of DNA with deoxyribonuclease I, phosphodiesterase, and alkaline phosphatase as described, for example, by Muller and Rajewsky in Muller R., and Rajewsky, M. F. Immunological quantification by high affinity antibodies of O$^6$-ethyldeoxyguanosine in DNA exposed to N-ethyl-N-nitrosourea. Cancer Res., 40: 887–896, 1980. The hydrolyzed DNA may be analyzed on a C$^{18}$-$\mu$ Bondapak reverse phase analytical high pressure liquid chromatography ("HPLC") column (Millipore, Milford, Mass.) with a linear gradient from 100% 100 mM phosphate buffer, pH 5.6, to 100% of 10% methanol in H$_2$O in 1 h at 1.5 ml/min. Fractions of 3 ml may be collected. The fractions may be lyophilized and reconstituted in 500 $\mu$l of PBS containing 0.1% BSA and tested for structures 1$a$ and 1$b$ using the competitive ELISA described above.

Fluorescene Assay. To analyze the in vitro modified calf thymus DNA, 2.8 mg of DNA were enzyme hydrolyzed and analyzed by HPLC as described above. The fractions containing structures 1a and 1b were concentrated to 1 ml and analyzed by HPLC with a Partisil SCX column, using isocratic elution with 1 mM ammonium phosphate buffer, pH 2.0, at 1 ml/min. The effluent was monitored with a Perkin-Elmer Corp. (Norwalk, Conn.) 650-10S fluorescene spectrophotometer. Concentration was determined by comparison of the fluorescene intensity to that of a synthetic standard.

EXPERIMENTAL RESULTS

Figure 2B:
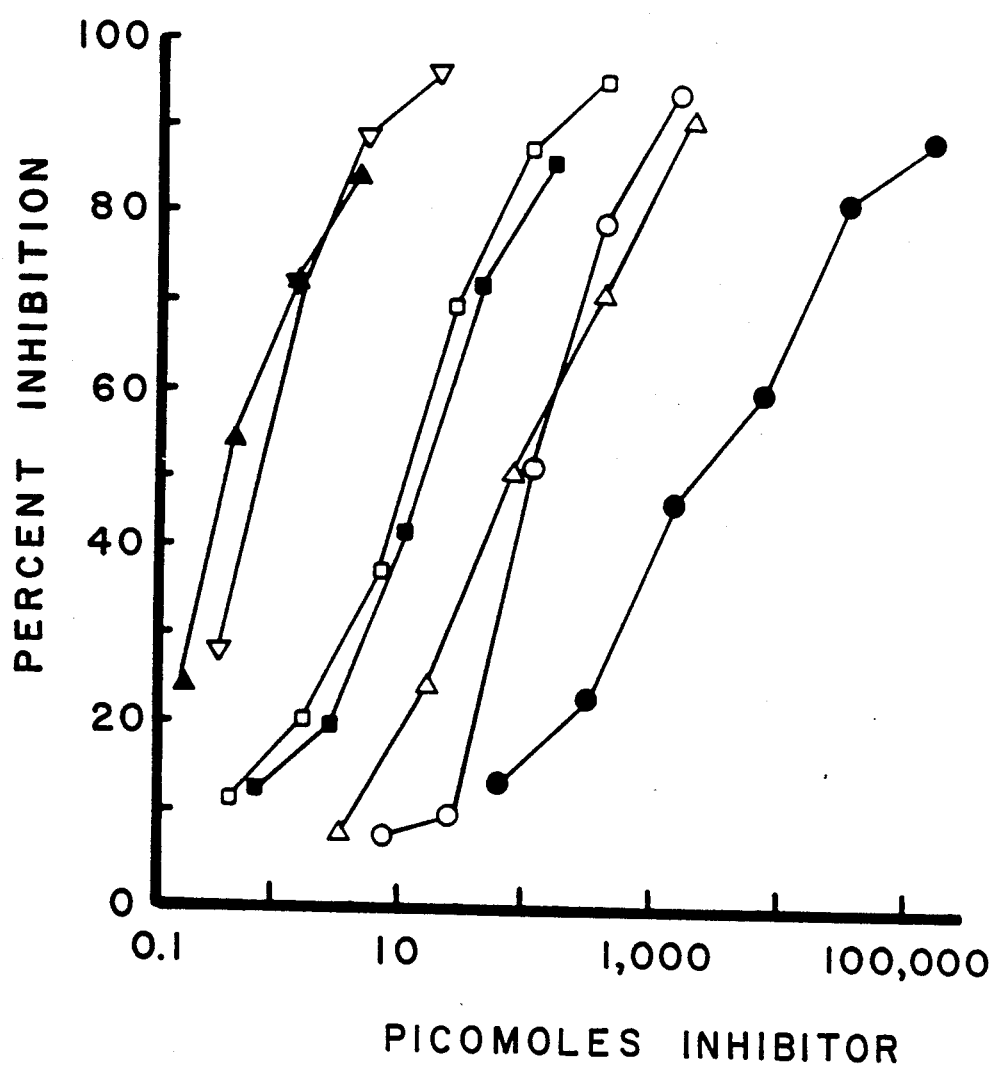

Using the above-identified procedures, a single mouse was boosted with the structure 1a,b-KLH conjugate for 4 consecutive days and the fusion was performed on the fifth day. Fourteen days after fusion, 113 of 288 wells showed growth of hybrid colonies. Thirteen of these wells, when tested in the ELISA, showed reactivity with structure 1a,b-KLH conjugate, in the presence of free KLH. For 4 of these 13 wells this binding could be inhibited with a mixture of structures 1a and 1b. These cell lines were cloned and named CA1, and CA2, CA3, and CA4. (These correspond to the cell lines deposited with the American Type Culture Collection and named HB9621; HB9622; HB9623 and HB9624, respectively.) The immunoglobulin isotypes of these antibodies were found to be: CA1, IgG2a; CA2, IgG2b; CA3 and CA4, IgG1. Their binding specificities were determined by competitive ELISA (Table 1; FIG. 2.) FIG. 2A shows inhibition of antibody CA3 in the competitive ELISA and FIG. 2B shows inhibition of antibody CA1 by ■ structure 1a; ▲, structure 1b; △, structure 2a; ▼, structure 2b; □, structure 1a,b base; o, structure 3; ●, deoxyguanosine.

The reactivity of the four antibodies was clearly strongest for structures 1a and 1b. Cross-reactivity was also seen with the free base form of structure 1 and with structures 1c, 1d and 1e. Of the normal DNA bases only deoxyguanosine showed significant cross-reactivity, particularly in the case of CA3. The remaining normal bases were unreactive. The antibodies were also unreactive with 2 methylated bases, $N^7$- and $O^6$-methyldeoxyguanosine, with the exception of CA3 and $O^6$-methyldeoxguanosine. These results suggest that CA3 is most specific for the hydroxyl group at position 8 of the modified deoxyguanosine, since the 3 most reactive molecules, structures 1b, 1d, and 1a all have the hydroxyl at position 8. Adduct 1c with the hydroxyl at position 6 is less reactive than the above three molecules. CA3 appears to have the same specificity except that it prefers the hydroxyl group in the opposite stereochemical configuration. The specificity of antibody CA2 is unique in that it is most specific for structure 1d which is formed from acrolein.

For the development of the immunoassay for structures 1a and 1b in DNA two antibodies were chosen; CA1 because of its high apparent affinity for structure 1b and CA3 because it had the highest affinity of the four antibodies for structure 1a. Because of the cross-reactivity of these antibodies for deoxyguanosine it was necessary to purify the DNA hydrolysate by HPLC prior to ELISA. FIG. 3 shows a chromatogram obtained by HPLC analysis of calf thymus DNA, which had been modified in vitro with crotonaldehyde and enzyme hydrolyzed. More specifically, it shows HPLC analysis of 2 mg of calf thymus DNA containing 168 mol of structures 1a and 1b per mol of deoxyguanosine.

Figure 3B:
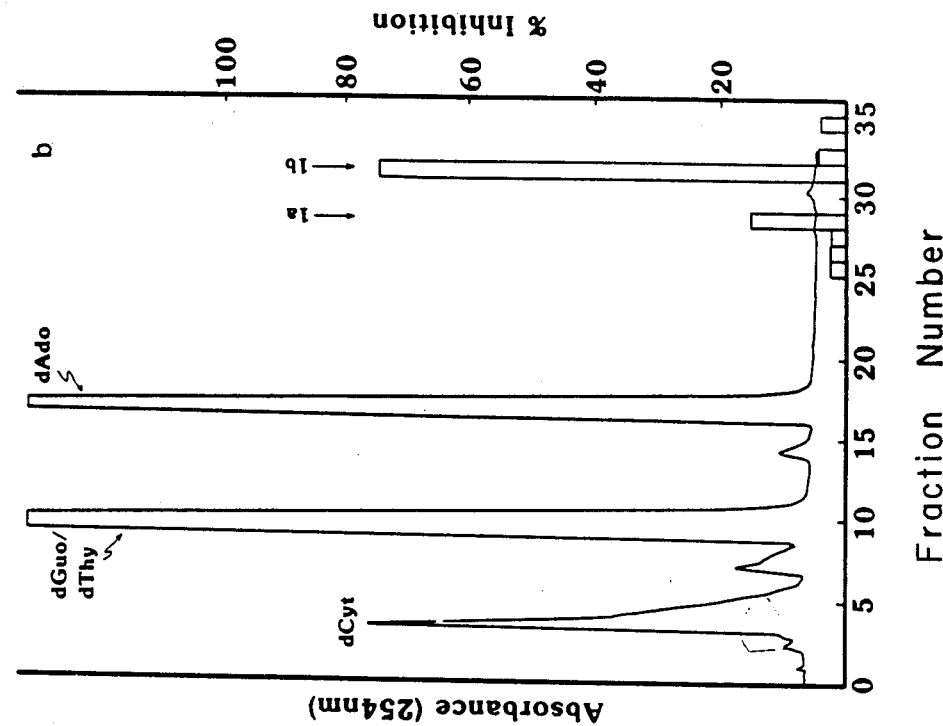
FIG. 3 comprises chromatograms 3A and 3B showing the results of immunoassays for structures 1a and 1b using antibodies produced using the process of the invention.
Figure 3A:
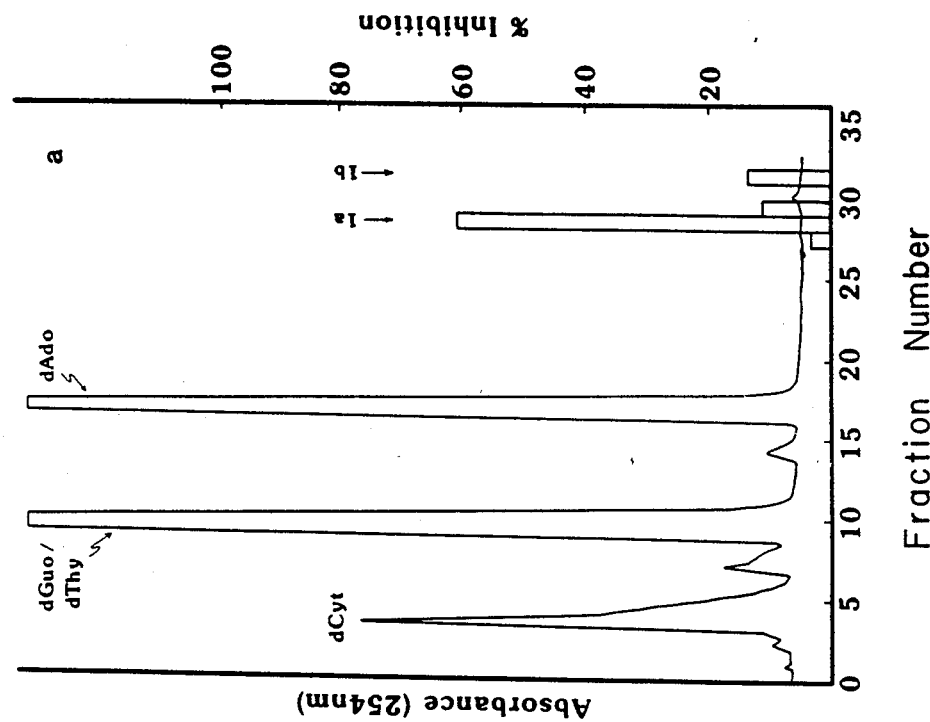

The sample was enzyme hydrolyzed and analyzed on reverse phase HPLC as described above. Fractions 26 thru 35 were tested in the ELISA with antibodies CA1 (FIG. 3A) and CA3 (FIG. 3B). In FIGS. 3A and 3B, the following abbreviations as used: dAdo, deoxyadenosine; dCyt, deoxycytidine; dGuo, deoxyguanosine; dThy, deoxythymidine. The compounds 1a and 1b elute in fractions 29 and 32 under these conditions. Fractions 26 through 35 were lyophilized, reconstituted, and tested in the ELISA. The results of these assays (FIG. 3) show that antibody CA3 was reactive only with material from fraction 29 which contains structure 1a. The low level of reactivity with fraction 32 which contains structure 1b is consistent with the cross-reactivity of CA3 with structure 1b (see Table 1). Analogous results were obtained with antibody CA1. The strongest reactivity occurred with fraction 32, with a lower level of reactivity with fraction 29. This is consistent with the specificity pattern of CA1 which has the highest affinity for structure 1b and lower affinity for structure 1a. To verify the accuracy of the assay for structures 1a and 1b, calf thymus DNA which had been modified in vitro with crotonaldehyde was analyzed for structures 1a and 1b by HPLC-fluorescence. A series of dilutions of modified DNA in unmodified DNA were made and the resulting samples were tested by HPLC-ELISA. The results of this analysis are shown in Table 2. The two methods are in good agreement. There is a linear relationship between the calculated level of DNA modification and the results of the ELISA with correlation coefficients of 0.987 and 0.997 for structures 1a and 1b, respectively. The theoretical sensitivity of this assay, based on the inhibition data, is 0.5 µmol structures 1a or 1b per mol deoxyguanosine. While it appears that structures 1a and 1b are formed in nearly equal amounts in vitro, the ability to assay for each isomer separately will allow one skilled in the art to determine if either is formed or removed preferentially in vivo.

Although the present invention has fully been decribed in connection with a preferred embodiment thereof, it is to be noted that various changes and modifications may be apparent to those skilled in the art. Such changes and modifications are to be understood as included within the true scope of the present invention as defined by the following claims.

TABLE 1

| Compound | Monoclonal antibody specificity | | | |
| --- | --- | --- | --- | --- |
|  | CA1 | CA2 | CA3 | CA4 |
| 1a[a] | 12.8[b] | 17 | 0.2 | 10 |
| 1b[c] | 0.2 | 0.4 | 10 | 0.9 |
| 1,base | 8.6 | 69 | 143 | 30 |
| 1c | 90 | 9 | 5 | 112 |
| 1d | 0.8 | 0.2 | 0.9 | 7.9 |
| 1e | 113 | 156 | 22 | 41,470 |
| Deoxyguanosine | 2,564 | 698 | 14 | 5,370 |
| Deoxyadenosine | >80,000 | >80,000 | >80,000 | >80,000 |
| Deoxycytosine | >110,000 | >110,000 | >110,000 | >110,000 |
| Thymidine | >100,000 | >100,000 | >100,000 | >100,000 |
| O-Methyldeoxy-guanosine | 56,790 | 51,270 | 235 | >100,000 |
| 7-Methylguanosine | >50,000 | >50,000 | >50,000 | >50,000 |

[a]The absolute configuration of the diastereomers 1a and 1b are not known. The configuration shown in FIG. 1 are arbitrary.
[b]Values are pmol of compound needed for 50% inhibition of binding in the competitive ELISA.
[c]A single isomer is obtained by acid hydrolysis of structures 1a and 1b.

TABLE 2

Comparison of fluorescene and immunoassay data of structures 1a and 1b in DNA

| mol/mol deoxyguanosine | | | |
|---|---|---|---|
| Fluorescene | | Immunoassay[a] | |
| 1a | 1b | 1a | 1b |
| 0 | 0 | 0 | 0 |
| 1 | 0.7 | 3.4 | 1.1 |
| 10.1 | 6.7 | 11.1 | 12.3 |
| 50.3 | 33.6 | 41.0 | 34.9 |
| 100.8 | 67.2 | 61.6 | 72.3 |

[a] Mean of duplicate determinations.

What is claimed is:

1. Monoclonal antibodies recognizing at least one of the 8R, 6R- and 8S, 6S stereoisomers of 3-(2-deoxy-β-D-erythropentofuranosyl)-5, 6, 7, 8-tetrahydro-8-hydroxy-6-methylpyrimino (1, 2-a) purine-10(3H)one produced by a hybridoma cell line selected from the group consisting of HB9621; HB9622; HB9623; and HB9624.

2. Antibody producing hybridoma cell lines characterized by the production of monoclonal antibodies recognizing cyclic deoxy deoxyguanosine adducts, said cell lines selected from the group consisting of HB9621; HB9622; HB9623; and HB9624.

3. A process for assaying a sample of DNA for the presence of cyclic deoxyguanosine adducts comprising hydrolyzing the DNA with at least one enzyme, purifying the hydrolyzed DNA, reacting the hydrolyzed and purified DNA with a monoclonal antibody produced by at least one of the hybridoma cell lines selected from the group consisting of HB9621; HB9622; HB9623; and HB9624, and testing for the presence of antibody-adduct complexes.

* * * * *